United States Patent
Cunningham

(10) Patent No.: US 7,186,293 B2
(45) Date of Patent: Mar. 6, 2007

(54) AGGLOMERATED STARCH COMPOSITIONS

(75) Inventor: Charles R. Cunningham, Ambler, PA (US)

(73) Assignee: BPSI Holdings, Inc., Wilmington, NJ (US)

( * ) Notice: Subject to any disclaimer, the term of this patent is extended or adjusted under 35 U.S.C. 154(b) by 0 days.

(21) Appl. No.: 11/376,855

(22) Filed: Mar. 16, 2006

(65) Prior Publication Data

US 2006/0216348 A1 Sep. 28, 2006

Related U.S. Application Data

(60) Provisional application No. 60/664,447, filed on Mar. 23, 2005.

(51) Int. Cl.
  *C08L 3/02* (2006.01)
  *A61K 9/20* (2006.01)

(52) U.S. Cl. .................... 106/206.1; 424/452; 424/465

(58) Field of Classification Search ............. 106/206.1; 424/452, 465
  See application file for complete search history.

(56) References Cited

U.S. PATENT DOCUMENTS

| | | | |
|---|---|---|---|
| 3,622,677 A | 11/1971 | Short et al. | |
| 4,072,535 A | 2/1978 | Short et al. | |
| 5,164,014 A | 11/1992 | Brancq et al. | |
| 5,468,286 A * | 11/1995 | Wai-Chiu et al. ...... | 106/205.01 |
| 6,143,324 A | 11/2000 | Michaud et al. | |
| 6,184,213 B1 | 2/2001 | Lefevre et al. | |
| 6,322,818 B1 | 11/2001 | Rebier | |
| 6,455,069 B1 | 9/2002 | Michaud et al. | |
| 6,497,899 B2 * | 12/2002 | Thombre et al. ............ | 424/464 |
| 6,617,446 B1 * | 9/2003 | Papadopoulos et al. ..... | 536/102 |
| 6,846,497 B2 * | 1/2005 | Okoniewska et al. ....... | 424/464 |
| 6,893,589 B1 * | 5/2005 | Misselbrook ................ | 264/115 |
| 2002/0054905 A1 * | 5/2002 | Weisser et al. ............. | 424/465 |
| 2006/0008521 A1 * | 1/2006 | Zhang et al. ............... | 424/464 |

FOREIGN PATENT DOCUMENTS

JP  56-28606  7/1981

* cited by examiner

*Primary Examiner*—David M. Brunsman
(74) *Attorney, Agent, or Firm*—Lucas & Mercanti, LLP

(57) ABSTRACT

Agglomerated starch compositions containing native starch and pre-compacted starch powder is disclosed. The agglomerated starch compositions have superior flow and less pH sensitivity than simple blends of the two components at equivalent ratios.

19 Claims, 4 Drawing Sheets

AGGLOMERATED STARCH COMPOSITIONS

CROSS REFERENCE TO RELATED APPLICATION

This application claims the benefit of priority from U.S. provisional patent application No. 60/664,447 filed Mar. 23, 2005, the contents of which are incorporated herein by reference.

FIELD OF THE INVENTION

The field of this invention is improved starch compositions which may be used to prepare tablets and filled capsules in the pharmaceutical and related arts.

BACKGROUND

U.S. Pat. No. 5,164,014 discloses the preparation of a directly-compressible starch for use in the manufacture of tablets by a multi-step process. First, a starch paste is produced by slurrying native starch in water and heating the dispersion to about 85° C. Next, the starch paste is sprayed onto native starch during a granulation process. Finally, the resulting mixture is dried, ground and sieved to obtain granules having a mean particle size of 100 to 500 micrometers (a.k.a. microns). The amount of starch paste is 1–20% by weight of the binary composition.

U.S. Pat. No. 6,143,324 also discloses a free-flowing, directly-compressible starch. In this case, an aqueous slurry of native starch is first heated to about 62° C. in order to cause partial swelling of the starch granules without causing disruption of the starch granules. The slurry is then cooled and spray-dried to yield a free-flowing powder. The '324 process eliminates the step of forming an intermediate starch paste; however, protracted heating and cooling steps are still involved. The product so formed has a ratio of non-swollen birefringent granules (intact native starch) to swollen non-birefringent granules (gelatinized starch) of 1:5 to 5:1. U.S. Pat. No. 6,455,069 dislcoses tabletting compositions comprising the '324 free-flowing, directly-compressible starch and at least one other excipient.

U.S. Pat. No. 6,184,213 discloses a diluent and disintegrating starch composition, which is comprised of amylose-rich starch granules in a pre-gelatinized starch matrix. This composition is prepared by mixing conventional and amylose-rich native starch slurries, each about 35% by weight in water, heating and drying the resultant mixture at about 100° C. to obtain a paste, and, finally, grinding said paste. Some of the native starch is gelatinized during the heating and drying process to yield the gelatinized starch matrix.

U.S. Pat. No. 6,322,818 discloses the preparation of agglomerated, spherical particles by coating starch seeds with successive layers of starch granules and pre-gelatinized starch. In this process, solid starch seeds are "fluidized" in a fluid bed apparatus, and a slurry of pre-gelatinized starch and native starch granules is then layered or coated onto the seeds such that agglomerates with spherical shapes are obtained. The spherical particles of this disclosure are used as carrier materials. Active pharmaceutical ingredients and excipients are coated or "loaded" onto these carrier particles.

Japanese patent application JP 56-28606 relates to the preparation of granular potato starch. It discloses a process wherein potato starch is charged in a fluidizing granulator, and a solution of gelatinized potato starch is sprayed as a binder. The fluidized potato starch agglomerates and grows surrounding the binder-starch nucleus to obtain fine granular potato starch with an average particle size of 150 to 1,000 micrometers. The process disclosed relies on the preparation of an intermediate gelatinized potato starch solution by heating a dispersion of potato starch in water at 80° C.

Pre-compacted starch powders for use as binders and/or disintegrants in the manufacture of tablets by direct compression and as fillers for formulations supplied in hard gelatin capsules are described in U.S. Pat. Nos. 3,622,677 and 4,072,535. Pre-compacted starch powder is obtained by subjecting a non-gelatinized granular starch to physical compaction between steel rollers with the possible input of thermal energy. The pre-compacted starch powder shows the presence of sharp birefringent granules and non-birefringent fragments of granules as well as some aggregates of granules and fragments. After the compaction, the starch is ground and sieved to yield a free-flowing powder. Tablets and capsules comprising the '677 and '535 starches have the tendency to disintegrate more slowly in a neutral aqueous medium than in a low pH medium (e.g. pH 1.2).

OBJECTS AND SUMMARY OF THE INVENTION

It is an object of this invention to provide an agglomerated starch composition which has improved flow properties and disintegrates at substantially the same rate in media of varying pH.

It is a further object of this invention to produce said starch compositions by simpler and hence more economical processes than those disclosed in the prior art.

In one aspect of the invention there are provided agglomerated starch compositions comprising native starch and pre-compacted starch powder. The inventive, agglomerated starch compositions are prepared by one of two methods. The first method is comprised of: 1) fluidizing a mixture comprising native starch and pre-compacted starch powder; and 2) spraying a slurry comprising pre-compacted starch powder onto the fluidized mixture. The second method is comprised of: 1) producing an aqueous slurry of pre-compacted starch powder and native starch; and 2) subsequently spray drying the slurry. In both cases, agglomerated starch compositions are obtained that achieve the objects of this invention. Given what have been described as limited binding capacities and poor disintegration properties of pre-compacted starch powders ('324 patent; Column 2; Lines 61–63), it is surprising that pre-compacted starch powders can be used productively to meet the objects of this invention.

DETAILED DESCRIPTION OF THE INVENTION

Figure 1:
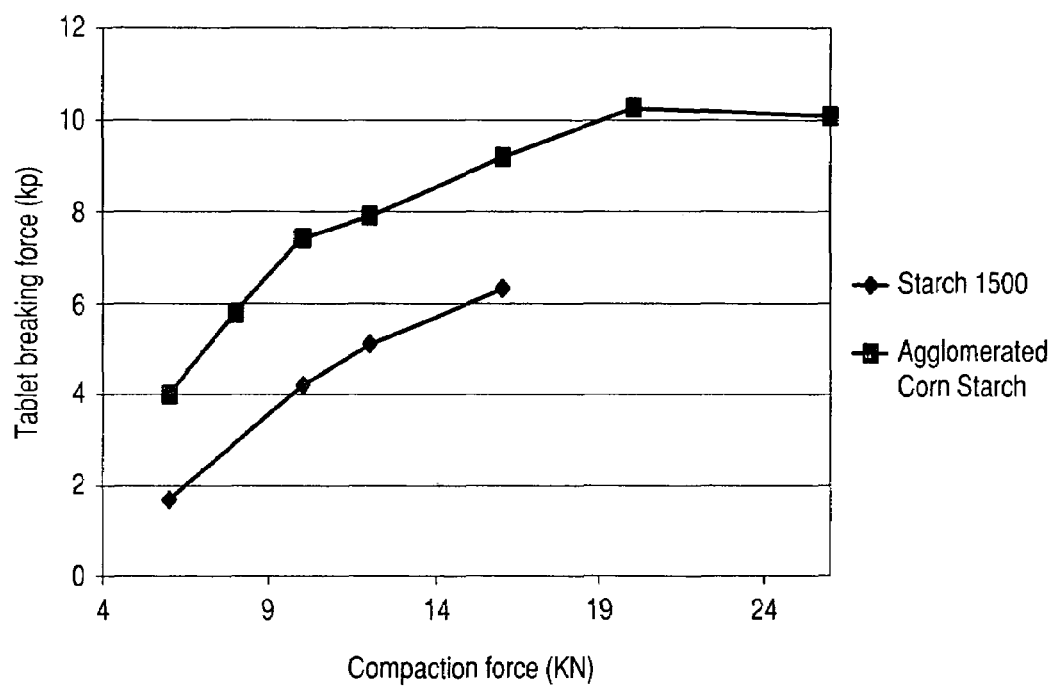
FIG. 1 shows the compaction profiles of tablets, prepared in Example 1.

The agglomerated starch compositions of this invention are comprised of native starch and pre-compacted starch powder. While Applicants are not bound by any specific theory, it is believed that the native starch and pre-compacted starch powder are physically bound together by intimately mixing the two components in the presence of water either via a wet granulation process or by forming a slurry and then spray drying. Despite prior art teachings to the contrary, pre-compacted starch powder effectively serves as a binder, which holds together native starch particles. Moreover, the native starch particles are bound by the pre-compacted starch powder in a substantially random manner resulting in agglomerated particles that have a range of sizes and shapes. Agglomerated starch compositions comprised of native starch and pre-compacted starch powder have significantly different properties than simple blends of the two components at equivalent ratios. Specifically, the agglomerated starch compositions have superior flow and less pH sensitivity than simple blends of the two components at equivalent ratios. Furthermore, the agglomerated starch compositions have flow rates of about 4.5 grams/second or higher as measured on a SOTAX FT300 flow tester and are substantially non-dusting.

Native starch refers to the starch that is derived directly from any one of a number of plant sources. Native starch is extracted from plant sources, with its granule structure remaining substantially intact, through a sequence of steps involving one or more of coarse milling, water washing, bleaching, wet sieving and centrifugal separation. The wet starch obtained from these processes is dried and milled before use in pharmaceutical formulations and the like. Native starch obtained in this manner is comprised of intact starch granules that are birefringent when photographed using polarized light. Suitable plant sources are maize or corn, potato, rice, tapioca and wheat. Native starch derived from corn is preferred.

Pre-compacted starch powder is manufactured according to known methods, including those disclosed in the aforementioned '677 and '535 patents. Preferably, pre-compacted starch powder is obtained by subjecting a non-gelatinized, granular, native starch to physical compaction between steel rollers with the possible input of thermal energy. After the compaction, the starch is ground and sieved to yield a free-flowing powder. The pre-compacted starch powder shows the presence of sharp birefringent granules and non-birefringent fragments of granules as well as some aggregates of granules and fragments, indicating that pre-compacted starch powder is a mixture of native starch and starch that has been modified in such a way that the original granule structure is changed. Pre-compacted starch powder is also characterized as a partially pre-gelatinized starch; however, this is distinguished from fully or completely pre-gelatinized starch, since a significant amount of intact native starch remains in the pre-compacted starch powder. Advantageously, aqueous dispersions prepared from pre-compacted starch powder have substantially lower viscosities than those prepared from completely pre-gelatinized starch at equivalent concentration. Suitable native starches useful for the preparation of pre-compacted starch powders are those derived from corn or maize, potato, rice, tapioca and wheat. Native corn starch is preferred for the preparation of pre-compacted starch powders. One particularly preferred, pre-compacted starch powder derived from corn is Starch 1500® manufactured by Colorcon.

The agglomerated starch compositions have a ratio of native starch to pre-compacted starch powder of from about 70:30 to about 99:1. Preferably, the ratio of native starch to pre-compacted starch powder is from about 85:15 to about 95:5. The average particle size of agglomerated starch compositions is from about 40 to about 200 micrometers. Preferably, the average particle size is from about 50 to about 120 micrometers. The agglomerated starch compositions may optionally comprise one or more additional excipients. For example, diluents, binding agents, binders, solubility enhancers, pH modulating agents, glidants, anti-adherents, flow aids, lubricants, disintegrants and mixtures thereof may be incorporated. In alternative aspects of this invention, the agglomerated starch compositions may also comprise active pharmaceutical agents or ingredients, vitamins, minerals and nutritional supplements. A non-limiting list of suitable pharmaceutical active agents includes:

a) Analgesics such as codeine, dihydrocodeine, hydrocodone, hydromorphone, morphine, diamorphine, fentanyl, buprenorphine, tramadol, oxycodone, acetaminophen, aspirin, phenylbutazone, diflunisal, flurbiprofen, ibuprofen, diclofenac, indomethacin, naproxen, methadone, meloxicam, piroxicam, or azapropazone;

b) Antihistamines such as loratidine, diphenhydramine, etc.;

c) Antihypertensives such as clonidine, terazosin, acebutalol, atenolol, propranolol, nadolol, nifedipine, nicardipine, verapamil, diltiazem, lisinopril, captopril, ramipril, fosinopril, enalapril, etc.;

d) Antibiotics such as democlocycline, doxycycline, minocycline, tetracycline, ciproflaxacin, amoxicillin, penicillin, erythromycin, metronidazole, cephalosporins, etc.;

e) Bronchial/anti-asthmatic agents such as terbutaline, salbutamol, theophylline, etc.;

f) Cardiovascular products such as procainamide, tocainide, propafenone, etc.;

g) Central nervous system agents/anti-anxiety agents/antidepressants such as levodopa, fluoxitene, doxepin, imipramine, trazodone, fluphenazine, perphenazine, promethazine, haloperidol, oxazepam, lorazepam, diazepam, clonazepam, buspirone, etc.;

h) Anti-cancer agents such as melfalan, cyclophosphamide, fluorouracil, methotrexate, etc.;

i) Anti-migraine products such as sumatriptan, lisuride, etc.;

j) Gastrointestinal agents such as cimetidine, ranitidine, omeprazole, misoprostol, etc.; and k) Oral anti-diabetic agents such as glipizide, gliboruride, etc.

The agglomerated starch composition may be prepared by: 1) fluidizing a mixture comprising native starch and pre-compacted starch powder; and 2) spraying a slurry comprising pre-compacted starch powder onto the fluidized mixture. Any standard fluid bed equipment may be utilized in this process so long as it is capable of allowing solid particles to be suspended in air while a liquid dispersion is applied. Fluid bed equipment supplied by Glatt is exemplary of suitable equipment for this purpose. In this method, the pre-compacted starch powder (about half of the total amount to be used) is first dispersed in water at a concentration of about 10% (w/w) with the aid of a mixer. Mixing is continued until the pre-compacted starch powder is substantially dispersed. Next, the remainder of the pre-compacted starch and all of the native starch is placed in the bowl of a fluidized bed apparatus. The dry ingredients in the bowl are then fluidized or suspended in air, and the aqueous slurry of pre-compacted starch is sprayed onto the particles. The inlet temperature is controlled at about 60° C. The resultant bed temperature is about 26–28° C. throughout the spray application process. Drying is conducted at about 70° C. until the bed temperature reaches about 40° C. The final product is a free-flowing agglomerated starch composition.

The agglomerated starch composition also may be prepared by: 1) producing an aqueous slurry of pre-compacted starch powder and native starch; and 2) subsequently spray drying the slurry. The slurry is produced by mixing all of the native starch and all of the pre-compacted starch powder in water. Any mixer may be utilized as long as a substantially homogeneous dispersion of the ingredients is obtained. The concentration of the combined ingredients in water is preferably about 40–50% (w/w). The viscosity of this slurry should have a viscosity less than about 2,000 centipoise to allow it to be readily pumped and atomized. Preferably, the viscosity of the slurry should be less than about 1,500 centipoise. The substantially homogeneous slurry is then transferred to an agitated hold tank. From the hold tank, the slurry is pumped into a spray dryer feed tank. The slurry is then transferred out of the feed tank by means of a pump to a homogenizer. The homogenizer supplies the slurry to a co-current spray dryer through a pressure nozzle. The slurry is then atomized and dried to the desired water content of 4–15% w/w, preferably 8–12% w/w, and an average particle size of 40–200 micrometers, preferably 50–120 micrometers, while operating the spray dryer within the following operating ranges:

Spray Dryer—Normal Operating Conditions

| Feed Pressure (psi) | 3,000–4,200 |
| Inlet Temperature (° F.) | 300–450 |
| Outlet Temperature (° F.) | 135–250 |
| Air Flow (CFM) | 8,000–12,000 |
| Feed Rate (GPH) | 200–250 |
| Temperature of Feed Slurry (° F.) | 70–120 |

The dry entrained material is then passed through a primary cyclone and combined with the material exiting the bottom of the dryer. This combined product is then conveyed to a packaging cyclone, isolated and sifted via a sifter containing a screen to yield the final agglomerated starch product having the flow characteristics described above. The screen size should be 12–40 mesh and preferably 14–30 mesh.

Of these two methods, the preparation of the agglomerated starch composition by: 1) producing an aqueous slurry of pre-compacted starch powder and native starch; and 2) subsequently spray drying the slurry is preferred due to the improved efficiency and economy derived from spray drying.

The inventive, agglomerated starch compositions may be used advantageously to manufacture a broad variety of orally-ingestible substrates. By way of illustration but not limitation, examples of said orally-ingestible substrates comprising the inventive agglomerated starch compositions include tablets and filled capsules, which preferably also comprise one or more active pharmaceutical ingredients, vitamins, minerals and/or other nutritional supplements, all of which are well known or will be readily apparent to those of ordinary skill. Standard methods of compressing tablets and filling capsules may be used to prepare said orally-ingestible substrates.

EXAMPLES

The following examples serve to provide further appreciation of the invention but are not meant in any way to restrict the effective scope of the invention.

Example 1

Manufacture and Characterization of Agglomerated Corn Starch

A fluid-bed process (3.0 kg) was used to agglomerate pure corn starch and pre-compacted corn starch powder that was prepared according to the processes described in the '677 and '535 patents (sold as Starch 1500® by Colorcon). The formulation consisted of 85% corn starch (Kingsford starch, a commercially available pure corn starch) and 15% Starch 1500. The agglomeration was performed in a Glatt GPCG-3 fluid bed with top-spray liquid delivery. Along with the entire amount of corn starch, half of the Starch 1500 was placed in the bowl and the remainder was dispersed in water at 10% solids concentration to be used as the binder.

The inlet temperature was controlled at 60° C. and the spray rate was 60–65 g/min. The resultant bed temperature was 26–28° C. throughout the spray application process. The actual spray time was 35 minutes. Drying was conducted at 70° C. until the bed temperature reached 40° C. (~12 minutes). The final product had an L.O.D. or water content of 8.5%. The material was free flowing.

Samples of the agglomerated starch were also tested for Brookfield viscosity at 10% solids concentration in both 0.1N HCl (pH 1.2) and pH 6.8 phosphate buffers. The agglomerated starch had a viscosity of less than 10 centipoise at both pH 1.2 and 6.8; whereas, the Starch 1500 had a viscosity of 25–40 centipoise and 40–90 centipoise at pH 1.2 and 6.8, respectively.

A compaction profile shown in FIG. 1 was run on the agglomerated starch material and compared to a compaction profile of the Starch 1500 batch that was used in the actual agglomeration process. The weight of the starch tablets was 225 mg. The agglomerated starch material showed much higher compactibility than the lot of Starch 1500.

Example 2

Polarized Light Microscopy

Figure 2A:
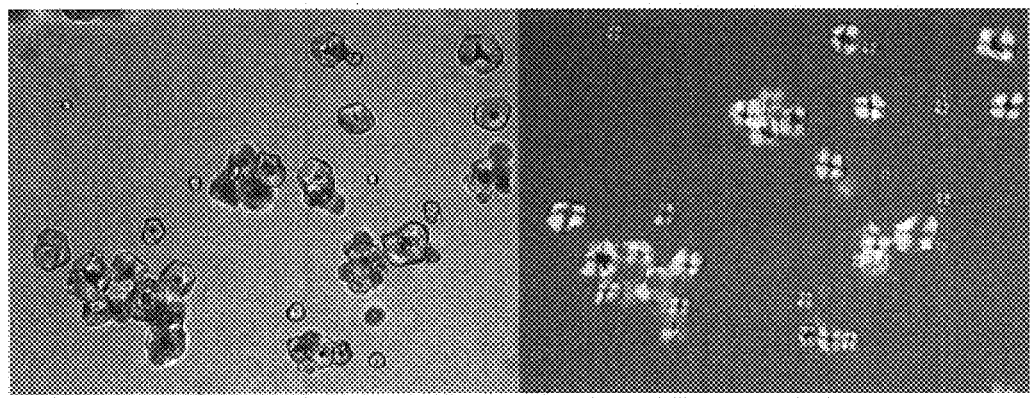
FIG. 2 shows the degrees of birefringence under polarized light microscopy for powders discussed in Example 2, wherein (A) is Native Corn Starch (Staley); (B) is Pre-compacted Corn Starch Powder (Starch 1500); and (C) is Agglomerated Corn Starch of Example 1.
Figure 2B:
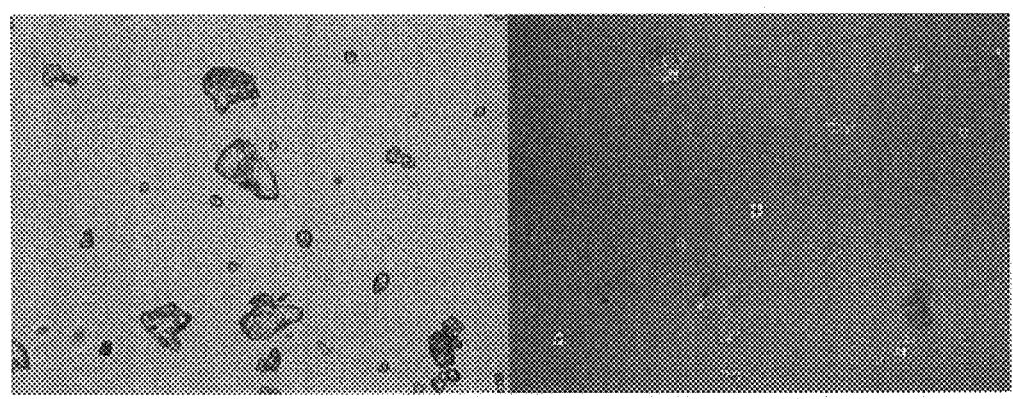
Figure 2C:
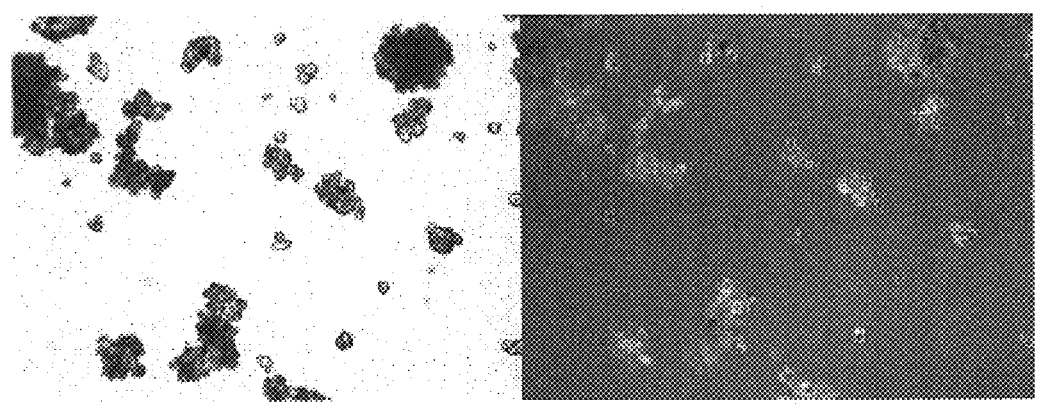

In order to further characterize the differences between native corn starch, pre-compacted corn starch powder (Starch 1500) and the agglomerated starch product, several samples were examined by polarized light microscopy. Native, intact starch grains exhibit a high degree of birefringence under polarized light. The photos shown in FIG. 2 compare the degree of birefringence of native corn starch (A), Starch 1500 (B), and the agglomerated starch (C). All samples were prepped in 1.660 refractive index oil. Starch 1500 in FIG. 2(B) contains both birefringent intact corn starch granules and non-birefringent glassy particles. Both native corn starch in FIG. 2(A) and the agglomerated starch product in FIG. 2(C) show a high percentage of intact granules that are birefringent. The picture of the agglomerated starch product shows that granules remain intact during the agglomeration process.

Example 3

Propranolol HCl Capsules Containing Agglomerated Corn Starch

Figure 3:
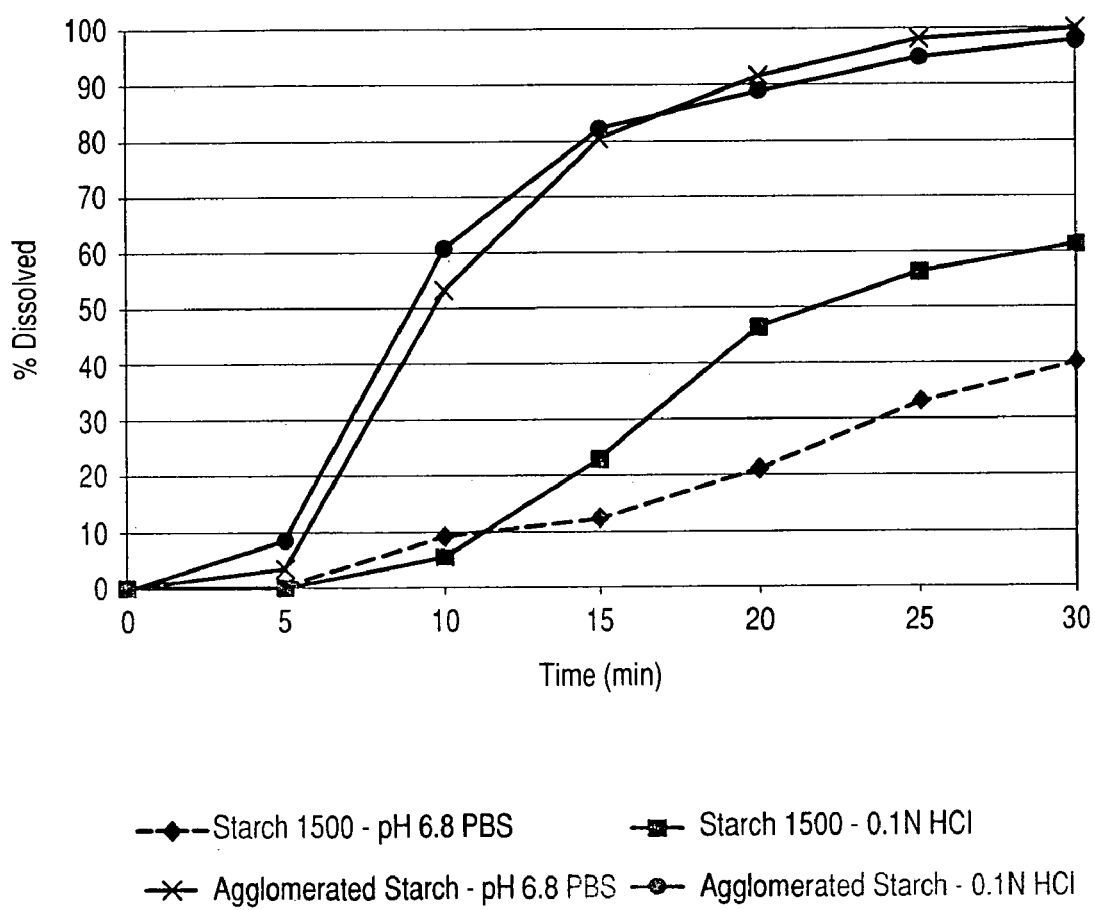
FIG. 3 shows dissolution profiles for propanolol HCl capsules discussed in Example 3.

Hard gelatin capsules (Size 1) were filled with blends of 25% propranolol HCl and 75% of either pre-compacted corn starch (Starch 1500) or the agglomerated corn starch of Example 1. Dissolution testing in FIG. 3 was done in 0.1N HCl (pH 1.2) or pH 6.8 phosphate buffer.

The capsules filled with the agglomerated corn starch showed very fast release in either the 0.1N HCl or the pH 6.8 phosphate buffer, while the capsules containing Starch 1500 were slower in the acid media and even slower in the pH 6.8 media.

The capsules containing the agglomerated starch product of Example 1 are much less sensitive to pH than those containing pre-compacted starch powder.

Comparative Example A

Pre-Compacted Corn Starch Powder/Native Corn Starch Blends

Figure 4:
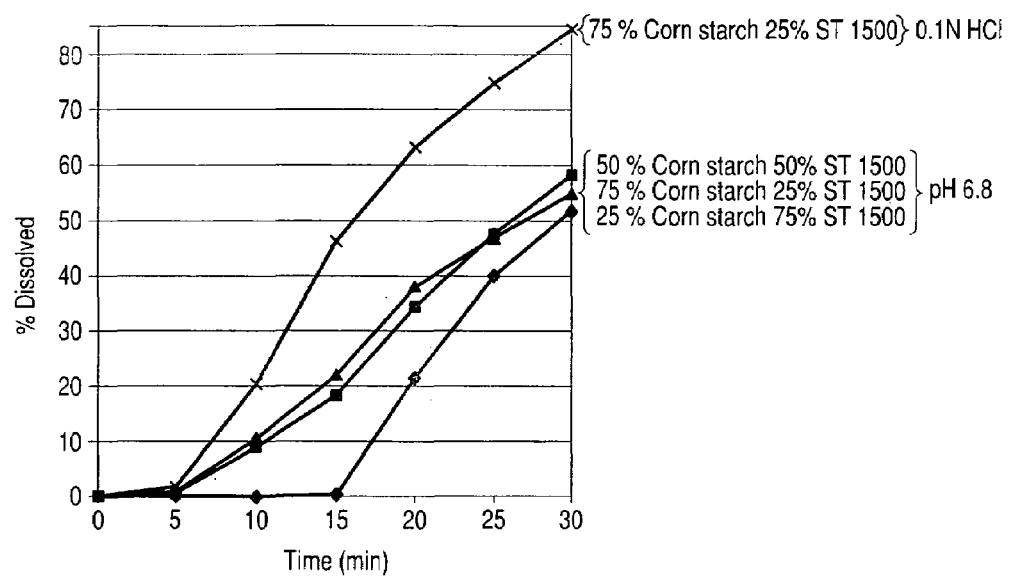
FIG. 4 shows a comparative dissolution profile for propanolol HCL capsules discussed in comparative Example A.

Referring to FIG. 4, an experiment was conducted using pre-compacted corn starch powder (Starch 1500)/native corn starch blends to determine whether simple blends could achieve the same results as the agglomerated starch product. As in Example 3, the capsule formulations contained 25% propranolol HCl and 75% Starch 1500/corn starch blends (non-agglomerated in this comparative example). The results show that with even as much as 75% corn starch in the formulation, dissolution was still depressed in pH 6.8 media.

Example 4

Large Scale Manufacture of Agglomerated Corn Starch

A slurry of corn starch NF and pre-compacted corn starch powder (Starch 1500) was prepared as follows. First, USP Purified Water (2,442 kg) was added to a mixing tank. Native corn starch NF (1,650.9 kg) was then charged and mixed until dispersed. Starch 1500 (184.7 kg) was finally added, and the slurry was mixed until homogeneous. The concentration of total solids in water was about 43%, and the ratio of native corn starch to Starch 1500 was about 9:1. This slurry was then transferred to an agitated hold tank.

From the hold tank, the slurry was pumped into a spray dryer feed tank. The slurry was then transferred out of the feed tank by means of a pump to a homogenizer. The homogenizer supplied the slurry to a co-current spray dryer through a pressure nozzle. The slurry was atomized and dried to the desired moisture (8–12% w/w) and average particle size (50–120 micrometers) specifications, while operating the spray dryer within the following operating ranges:

Spray Dryer—Normal Operating Conditions

| Feed Pressure (psi) | 3,000–4,200 |
|---|---|
| Inlet Temperature (° F.) | 300–450 |
| Outlet Temperature (° F.) | 135–250 |
| Air Flow (CFM) | 8,000–12,000 |
| Feed Rate (GPH) | 200–250 |
| Temperature of Feed Slurry (° F.) | 70–120 |

The dry entrained material was then passed through a primary cyclone and combined with the material exiting the bottom of the dryer. The total spray drying time was about four hours. This combined product was then conveyed to a packaging cyclone, isolated and sifted via a sifter containing a 20 mesh screen to yield the final agglomerated starch product. The resulting product was a free-flowing powder determined to have similar characteristics to those described in Example 1.

Powder flow was measured using a SOTAX FT300 flow tester equipped with a standardized funnel and orifice having the following dimensions:

| Funnel diameter (top) | 14.5 cm |
|---|---|
| Funnel diameter (bottom) | 2.5 cm |
| Orifice width (bottom) | 5.5 mm |

The flow tester was operated using a standardized mixing cycle of two inversions (with the bottom orifice closed) followed by a pre-vibration cycle of 20 seconds. The funnel vibrated at an intensity setting of 3 while the orifice was open during the test. Under these conditions, a series of samples, pulled from separately packaged drums of the agglomerated starch composition, had average flow rates of 5.7 to 6.7 grams/minute. The powder also flowed with minimal dust being generated. In contrast, native corn starch had no discernible flow under the same conditions—i.e. a flow rate of 0. Pre-compacted corn starch had an average flow rate of 3.9 grams/minute under the same conditions and generated significantly more dust.

The high powder flow rate of the agglomerated starch composition is advantageous, because it allows the artisan to compress tablets and fill capsules rapidly on an industrial scale. The substantially non-dusting characteristics of agglomerated starch compositions are also considered advantageous, because clean up after capsule filling or tabletting operations is significantly easier than when dustier compositions are used.

Examples 5–7 and Comparative Example B

Variation of Native Corn Starch to Pre-Compacted Corn Starch Powder (Starch 1500) Ratios Agglomerated starches were produced according to the same process described in Example 4 except that the quantities and ratios of the raw materials were varied. These examples are summarized in the following table:

| Components | Ex. 5 | Ex. 6 | Ex. 7 | Comp. Ex. B |
|---|---|---|---|---|
| Deionized water (kg) | 719.2 | 719.2 | 638.5 | 319.1 |
| Native corn starch (kg) | 462.6 | 489.8 | 517.0 | 272.1 |
| Starch 1500 (kg) | 81.6 | 54.4 | 27.2 | 0.0 |
| Native corn starch to Starch 1500 ratio | 85:15 | 90:10 | 95:5 | 100:0 |
| Average particle size Malvern D[4,3] (micrometers) | 82.4 | 70.1 | 53.7 | 25.3 |

The products of Examples 4–6 were free-flowing powders that had characteristics similar to those of the product of Example 1. The product of Comparative Example B showed no evidence of agglomeration and had poor flow characteristics.

Example 8 pH Dependence of Tablet Disintegration Times

Each of the products obtained in Examples 5–7 were compressed into standard concave tablets (5/16"; tablet weight 225 mg) at 9 KN force. Six tablets of each type were immersed in 0.1 N HCl (pH 1.2), and the average disintegration times were measured. Six new tablets of each type were then immersed in pH 6.8 buffer, and the average disintegration times were measured. The disintegration times are compared in the following table.

Disintegration Times of Tablets Prepared from Pre-Compacted Corn Starch Powder (Starch 1500) and Agglomerated Corn Starches

|  | Tablet Components | | | |
| --- | --- | --- | --- | --- |
|  | Starch 1500 | Ex. 5 | Ex. 6 | Ex. 7 |
| Disintegration time in pH 1.2 (sec) | 665 | 334 | 186 | 109 |
| Disintegration time in pH 6.8 (sec) | 811 | 320 | 186 | 95 |
| Difference (sec) | 146 | 14 | 0 | 14 |

Tablets prepared from Starch 1500 alone disintegrate at significantly different rates in pH 1.2 and pH 6.8 media; whereas, tablets prepared from the agglomerated starches of Examples 5–7 have disintegration times that are relatively insensitive to pH. Therefore, agglomerated starch compositions can be used to prepare orally-ingestible substrates that have substantially the same disintegration rates in the variable pH environment of the gastrointestinal tract. This lack of pH sensitivity is also advantageous to insure that the release of the active pharmaceutical ingredient and the like is substantially the same in the fed and fasted states of the stomach, where it is known that the pH of the stomach varies considerably.

Each of the patents and publications mentioned in this application are incorporated herein by reference.

The invention claimed is:

1. An agglomerated starch composition comprising native starch and pre-compacted starch powder.

2. A composition according to claim 1, wherein said native starch is derived from corn.

3. A composition according to claim 1, wherein said pre-compacted starch is derived from corn.

4. A composition according to claim 1, wherein the ratio of native starch to pre-compacted starch powder is from about 70:30 to about 99:1.

5. A composition according to claim 1, wherein the ratio of native starch to pre-compacted starch powder is from about 85:15 to about 95:5.

6. A composition according to claim 1, wherein the average particle size is from about 40 to about 200 micrometers.

7. A composition according to claim 1, wherein the average particle size is from about 50 to about 120 micrometers.

8. A composition according to claim 1, wherein the agglomerated starch composition disintegrates at substantially the same rate in media with pH values from about 1 to about 7.

9. A composition according to claim 1, wherein the composition was manufactured by fluidizing a mixture comprising native starch and pre-compacted starch powder and spraying a slurry comprising pre-compacted starch powder onto the fluidized mixture.

10. A composition according to claim 1, wherein the composition was manufactured by producing a slurry comprised of native starch and pre-compacted starch powder and spray drying the slurry.

11. A composition according to claim 1, further comprising one or more excipients selected from the group consisting of diluents, binding agents, binders, solubility enhancers, pH modulating agents, glidants, anti-adherents, flow aids, lubricants, disintegrants and mixtures thereof.

12. A composition according to claim 1, further comprising an active pharmaceutical agent.

13. Orally-ingestible substrates comprising the composition of claim 1.

14. The substrates of claim 13, wherein the substrates disintegrate at substantially the same rate in media with pH values from about 1 to about 7.

15. The substrates of claim 13, wherein the substrates are tablets.

16. The substrates of claim 13, wherein the substrates are capsules.

17. The substrates of claim 13 further comprising one or more active pharmaceutical ingredients, vitamins, minerals or other nutritional supplements.

18. A method for producing an agglomerated starch composition comprising the steps of fluidizing a mixture comprising native starch and pre-compacted starch powder; and spraying a slurry comprising pre-compacted starch powder onto the fluidized mixture.

19. A method for producing an agglomerated starch composition comprising the steps of producing a slurry comprised of native starch and pre-compacted starch powder; and spray drying the slurry.

* * * * *

UNITED STATES PATENT AND TRADEMARK OFFICE
CERTIFICATE OF CORRECTION

| | | |
|---|---|---|
| PATENT NO. | : 7,186,293 B2 | |
| APPLICATION NO. | : 11/376855 | |
| DATED | : March 6, 2007 | |
| INVENTOR(S) | : Charles R. Cunningham | |

It is certified that error appears in the above-identified patent and that said Letters Patent is hereby corrected as shown below:

Title Page,
Item (73) "Wilmington, NJ" should read --Wilmington, DE--

Column 2, line 51, "(Staley)" should read --(Tate & Lyle)--

Signed and Sealed this

Fourteenth Day of August, 2007

JON W. DUDAS
*Director of the United States Patent and Trademark Office*